United States Patent
Marciniec et al.

(10) Patent No.: US 8,344,169 B2
(45) Date of Patent: Jan. 1, 2013

(54) VINYL-ALKYNYLSUBSTITUTED GERMANIUM COMPOUNDS AND METHOD TO OBTAIN VINYL-ALKYNYLSUBSTITUTED GERMANIUM COMPOUNDS

(75) Inventors: Bogdan Marciniec, Swarzedz (PL); Beata Dudziec, Poznan (PL)

(73) Assignee: Adam Mickiewicz University, Poznan (PL)

(*) Notice: Subject to any disclaimer, the term of this patent is extended or adjusted under 35 U.S.C. 154(b) by 0 days.

(21) Appl. No.: 13/395,378

(22) PCT Filed: Aug. 20, 2010

(86) PCT No.: PCT/PL2010/000077
§ 371 (c)(1),
(2), (4) Date: Mar. 9, 2012

(87) PCT Pub. No.: WO2011/031172
PCT Pub. Date: Mar. 17, 2011

(65) Prior Publication Data
US 2012/0178952 A1 Jul. 12, 2012

(30) Foreign Application Priority Data
Sep. 11, 2009 (PL) .......................................... 389013

(51) Int. Cl.
*C07F 7/08* (2006.01)
*C07F 7/30* (2006.01)

(52) U.S. Cl. ............................................ 556/12; 556/87
(58) Field of Classification Search .................... 556/12, 556/87
See application file for complete search history.

(56) References Cited

OTHER PUBLICATIONS

Billeb et al., "Chemistry of Heavy Carbene Analogues $R_2M$ (M=Si, Ge, Sn). Reactions of Free Dimethylgermylene with Alkynes and Their Palladium Catalysis," *Organometallics*, 1992, pp. 2069-2074, vol. 11, American Chemical Society.
Jan. 13, 2011 Written Opinion issued in International Patent Application No. PCT/PL2010/000077.
Jan. 13, 2011 International Search Report issued in International Patent Application No. PCT/PL2010/000077.

*Primary Examiner* — Porfirio Nazario Gonzalez
(74) *Attorney, Agent, or Firm* — Oliff & Berridge, PLC

(57) ABSTRACT

New vinyl-alkynylsubstituted germanium compounds having the general formula 1 are the subject of the invention. The invention also relates to a new method of obtaining vinyl-alkynylsubstituted germanium compounds having the general formula 1. — A denotes: diethylgermyl — R denotes: triethylsilyl, 1-(trimethylsiloxy)-1-cyclohexyl The invention also provides a solution to the problem of the method of obtaining vinyl-alkynylsubstituted germanium compounds having the general formula 1, involving the germylative coupling reaction between a suitable substituted terminal alkyne and a suitable divinylsubstituted germanium compound in the presence of a ruthenium(II) complex as catalyst.

6 Claims, No Drawings

VINYL-ALKYNYLSUBSTITUTED GERMANIUM COMPOUNDS AND METHOD TO OBTAIN VINYL-ALKYNYLSUBSTITUTED GERMANIUM COMPOUNDS

New vinyl-alkynylsubstituted germanium compounds having the general formula 1 are the subject of the invention. The invention also relates to a new method of obtaining vinyl-alkynylsubstituted germanium compounds having the general formula 1.

It was the purpose of the invention to make new vinyl-alkynylsubstituted germanium compounds and develop a simple method for their synthesis.

The essence of the invention are new, not previously known in the art, vinyl-alkynylsubstituted germanium compounds having the general formula 1 where

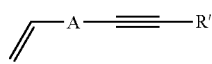  (1)

A denotes: diethylgermyl
R' denotes: triethylsilyl, 1-(trimethylsiloxy)-1-cyclohexyl The new compounds, as disclosed in the patent, are colorless or straw-colored, oily substances. The bifunctional vinyl-alkynylsubstituted organogermanium compounds of the invention may be applied in organometallic synthesis as reactants for obtaining known, organic germanium compounds. The presence of a double and a triple bond enables the compounds to be used in hydrometallation processes (e.g., hydrosilylation, hydrogermylation, hydroboronation, etc.) as reactants which may be applied in commercial processes as intermediates.

In the second aspect of the invention, the subject of the invention relates to a method of obtaining vinyl-alkynylsubstituted germanium compounds having the general formula 1 where A and R' denote the same as stated above, involving a germylative coupling reaction between a suitable substituted terminal alkyne having the general formula 2 where

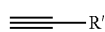  (2)

R' denotes the same as stated above,
and a suitable divinylsubstituted germanium compound having the general formula 3 where

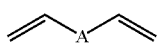  (3)

A denotes the same as stated above, in the presence of a ruthenium(II) complex as catalyst.

A [carbonylchlorhydridebis(tricyclohexylphosphine)ruthenium(II)] or [carbonylchlorhydridebis(triisopropylphosphine)ruthenium(II)] is used as a catalyst in the amount of 0.5-3.5% mol relative to alkyne, preferably in the amount of 2%.

The reaction is carried out under inert gas and in a solvent selected from a group of aromatic organic compounds, most preferably in toluene.

In the method of the invention, a mixture of a suitable divinylsubstituted germanium compound with a suitable terminal alkyne and catalyst is heated at a temperature not lower than 60° C. until completion of the reaction, and raw product is then refined.

The reaction proceeds at any ratio of the reactants, although a lot of byproducts are formed at unfavorable ratios. If equimolar quantities of the alkyne and the divinylsubstituted germanium compound are used the selectivity of the process drastically lowers and products of the terminal alkyne dimerization—which is a competitive and parallel reaction—are observed in the post-reaction mixture in addition to the desirable product. If the system contains a stoichiometric excess of divinylgermane, then the selectivity of the process favors the formation of the desirable reaction product, i.e., vinyl-alkynylsubstituted germanium compound, while the alkyne dimerization reaction does not occur at all. If the excess of the divinylsubstituted germanium compound is too high, its homo-coupling reaction is favored which affects the overall process yield and selectivity. The reaction of the invention is preferably performed at a 1.2 to 3-fold excess by mole of the vinylsubstituted germanium compound relative to the terminal alkyne.

The reaction of the invention is carried out at a temperature in the range 60-130° C., preferably 110-120° C.

Generally, the reaction time is 18-48 hrs, preferably 48 hrs.

The synthesis of the invention is carried out in a reactor which is protected from moisture, equipped with a reflux condenser, a mixing device and in an inert gas atmosphere, most preferably argon. The reactor is filled, in the following order, with: catalyst, solvent, divinylsubstituted germanium compound, and then the alkyne. All of the liquid reactants as well as the solvent ought to be dewatered and deoxidized because of the sensitivity and decomposability of the catalyst in the presence of any traces of water and oxygen. The reaction mixture is then heated and mixed until the reaction is complete.

Reversing the order in which the reactants are introduced, i.e., first the alkyne, then the divinylsubstituted germanium compound is also possible though it potentially reduces the selectivities of the process, specifically, alkyne dimerization products are then formed.

Raw product is separated and refined. Usually, such separation consists of evaporation of the solvent from the post-reaction mixture and any residual unreacted reactants, followed by purification of the raw product from the catalyst on a chromatographic column filled with silica gel or silica gel modified with 15% $Et_3N$, using aliphatic hydrocarbons, preferably hexane or pentane, as eluent. Distillation may be used as a variant of the separation and refining of the raw products, although due to their high boiling ranges, it is preferably effected at reduced pressures. Product decomposition in the distillation process may occur in some cases.

The subject of the invention is shown by way of examples, which are intended to illustrate rather than limit the scope of the invention.

EXAMPLE I

In a 10 mL reactor, equipped with a reflux condenser and stirrer, filled with an inert gas, a 0.04 g carbonylchlorhydridebis(tricyclohexylphosphine)ruthenium(II) is placed and then, in the following order, 3.99 mL toluene, 1.02 g diethyldivinylgermane and 0.39 g triethylsilylethyne are added. The reaction mixture was heated at 110° C. for forty eight hours. Conversion of the terminal alkyne and raw product yield were 64%. The structure of the product was confirmed by GCMS analysis.

MS (EI) m/z (rel. int. %): 299 (7) [M⁺+H], 269 (60) [M⁺—CH$_2$CH$_3$], 240 (18), 235 (100), 211 (12), 169 (22), 144 (42), 131 (41), 117 (26), 91 (54), 79 (21), 65 (12)

EXAMPLE II

As in reaction conditions of Example I, to 3.99 mL of toluene, the 0.04 g of carbonylchlorhydridebis(tricyclohexylphosphine)ruthenium(II) is added and the reaction was carried out between 1.02 g of diethyldivinylgermane and 0.54 g 1-ethynyl-1-(trimethylsiloxy)cyclohexane. Conversion of the terminal alkyne and raw product yield was 65%. In order to remove the catalyst from the system, the solvent and any residual unreacted reactants were evaporated from the post-reaction mixture and the whole material was transferred onto a chromatographic column filled with silica gel modified with a triethylamine, wherafter product was separated, using hexane as eluent. The product, 1-[{diethylvinylgermyl}ethynyl]-1-(trimethylsiloxy)cyclohexane, was obtained at a yield of 55%, in the form of an oily liquid with a light straw color. The product structure was confirmed by $^1$H, $^{13}$C NMR and GCMS analyses.

$^1$H NMR (CDCl$_3$) δ (ppm): 0.18 (s, CH$_3$SiO); 0.91-093 (m, GeCH$_2$CH$_3$); 1.07-1.10 (tr, GeCH$_2$CH$_3$); 1.21-2.48 (m, (C$_6$H$_{10}$)C≡); 5.76-5.84 (dd, J$_{H,H}$=4 Hz, 19 Hz, 1H, H$_2$C=CHGe); 6.01-6.07 (dd, J$_{H,H}$=4 Hz, 13 Hz, 1H, H$_2$C=CHGe); 6.14-6.25 (dd, J$_{H,H}$=13 Hz, 19 Hz, 1H, H$_2$C=CHGe)

$^{13}$C NMR (CDCl$_3$) δ (ppm): 1.05 (CH$_3$SiO); 6.62 (GeCH$_2$CH$_3$); 8.85 (GeCH$_2$CH$_3$); 22.31-70.48 ((C$_6$H$_{10}$)C≡); 85.77, 110.97 (C≡C); 132.16 (CH$_2$=CHGe); 134.67 (CH$_2$=CHGe)

MS (EI) m/z (rel. int. %): 355 (10) [M⁺+H], 325 (5) [M⁺—CH$_2$CH$_3$], 253 (18), 235 (100), 225 (12), 169 (25), 147 (40), 133 (44), 119 (27), 91 (52), 79 (28), 65 (14)

The invention claimed is:

1. New vinyl-alkynylsubstituted germanium compounds having the general formula 1 where

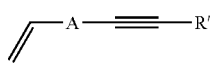
(1)

A denotes: diethylgermyl
R' denotes: triethylsilyl, 1-(trimethylsiloxy)-1-cyclohexyl.

2. A method to obtain vinyl-alkynylsubstituted germanium compounds having the general formula 1 where

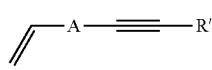
(1)

A denotes: diethylgermyl
R' denotes: triethylsilyl, 1-(trimethylsiloxy)-1-cyclohexyl, wherein a germylative coupling reaction occurs between a suitable substituted terminal alkyne having the general formula 2 where

(2)

R' denotes the same as stated above, and a suitable divinyl-substituted germanium compound having the general formula 3 where

(3)

A denotes the same as stated above, in the presence of a ruthenium(II) complex as catalyst.

3. A method as claimed in claim 2 wherein [carbonylchlorohydridebis(tricyclohexylphosphine)ruthenium(II)] or [carbonylchlorohydridebis-(triisopropylphosphine)ruthenium (II)] is used as catalyst.

4. A method as claimed in claim 3 wherein [carbonylchlorohydridebis(tricyclohexylphosphine)ruthenium(II)] is used as catalyst.

5. A method as claimed in claim 4 wherein the catalyst is used in the amount of 0.5-3.5% mol relative to alkyne.

6. A method as claimed in claim 5 wherein the catalyst is used in the amount of 2%.

* * * * *